United States Patent [19]

Gerstein

[11] Patent Number: 4,714,610

[45] Date of Patent: Dec. 22, 1987

[54] LOW PH HAIR CONDITIONER COMPOSITIONS CONTAINING AMINE OXIDES

[75] Inventor: Terry Gerstein, Brunswick, N.J.

[73] Assignee: Revlon, Inc., New York, N.Y.

[21] Appl. No.: 814,105

[22] Filed: Dec. 27, 1985

Related U.S. Application Data

[63] Continuation-in-part of Ser. No. 632,745, Jul. 20, 1984, abandoned, which is a continuation-in-part of Ser. No. 406,668, Aug. 9, 1982, abandoned.

[51] Int. Cl.[4] .............................................. A61K 7/075
[52] U.S. Cl. ..................................................... 424/70
[58] Field of Search .................. 424/70; 252/DIG. 13

[56] References Cited

U.S. PATENT DOCUMENTS

| | | | |
|---|---|---|---|
| 3,098,794 | 7/1963 | Dohr et al. | 424/70 |
| 3,483,178 | 12/1969 | Crutchfield et al. | 424/70 |
| 3,637,682 | 1/1972 | Gerecht | 424/70 |
| 3,842,847 | 10/1974 | Hewitt et al. | 424/70 |
| 3,943,234 | 3/1976 | Roggenkamp | 514/724 |
| 4,007,261 | 2/1977 | Sorrentino et al. | 424/70 |

OTHER PUBLICATIONS

Harry's Cosmeticology, Seventh edition, 1982, p. 516.

*Primary Examiner*—Johnnie R. Brown
*Assistant Examiner*—Jacqueline M. Stone
*Attorney, Agent, or Firm*—Hoffmann, Dilworth, Barrese & Baron

[57] ABSTRACT

Disclosed herein are improved cationic hair conditioning compositions comprising an amine oxide and, water and sufficient acid to provide a pH for said composition of from about 3.8 to about 2.4 and an amine oxide concentration from about 0.5% to about 10% based on the total weight of said hair conditioning composition.

17 Claims, No Drawings

LOW PH HAIR CONDITIONER COMPOSITIONS CONTAINING AMINE OXIDES

CROSS-REFERENCE TO RELATED APPLICATIONS

This application is a continuation-in-part of commonly assigned, copending U.S. patent application Ser. No. 632,745, filed July 20, 1984 now abandoned which in turn is a continuation-in-part of commonly assigned U.S. patent application Ser. No. 406,668, filed Aug. 9, 1982, now abandoned.

BACKGROUND OF THE INVENTION

This invention relates to hair conditioning compositions. More particularly, this invention relates to aqueous hair conditioning compositions that comprise relatively high molecular weight amine oxides at low pH's.

Hair conditioning agents assist in the control and management of hair. Conditioned hair is easily untangled and combed through after shampooing, lays orderly when dry and provides a favorable feeling to the touch. The conditioning action on hair, particularly by cationic conditioning agents, is believed to be caused by the attraction of the positively charged agent to the negative sites on hair protein resulting in the deposition of the agent onto the hair fiber.

After washing hair and during the subsequent management of the dry hair, the combing and brushing forces produce friction resulting in the accumulation on the hair's surface of immobile electrons or ions of the same charge. The hair is commonly referred to as containing static charge and displays the phenomenon of "fly-away". Such hair is unruly, will not lay flat and is considered generally unmanageable.

Ionic depositions including positively charged cationic conditioning agents can be used to dissipate static electricity by increasing the mobility of the electrostatic charges that accumulate on hair. Furthermore, the fatty nature of the cationic conditioning agent produces lubrication on the hair's surface that reduces friction resulting in both the overall lessening of accumulated electrostatic charges and the promotion of easy combing. The process by which cationic surfactants are applied to hair is referred to as conditioning the hair, and the treatment results in hair that no longer sustains a static charge and in hair that also feels soft, silky and is highly manageable.

Cationic surfactants have been used extensively as hair conditioning agents in creme rinses and shampoos, generally at pH levels below pH 7 in creme rinses and through pH 7 and above in shampoos. In the past, best results in creme rinses have been obtained with cationic surfactants that are long chain high molecular weight quaternary ammonium compounds or long chain fatty amine salts. For example, stearalkonium chloride has been widely used as a component of creme rinse hair conditioning formulations. The positive charge of the quaternary surfactant is attracted to the negatively charged surface of the hair protein; the surfactant deposits on the surface and subsequently renders the hair manageable. The long chain constituent on the quaternary surfactant coats the hair fiber giving it lubricity during wet combing and a desirable texture after drying. The longer the chain length the more active the conditioning agent is said to be; the greater the residual film deposit on hair the easier the detangling effort and the less electrostatic charge build-up and subsequent hair fly-away.

Quaternary ammonium compounds carry and maintain positive ionic charges from highly alkaline to highly acidic media. However, many industrial quaternary ammonium compounds are partially or totally unsuitable for cosmetic use because they can contain impurities which restrict use to specific pH ranges or restrict use completely. If trace quantities of deleterious quaternizing agents used in synthesis are present, the quaternary ammonium compound should not be used in cosmetics. Long chain fatty amines, which usually account as significant impurity in the quaternary ammonium compounds used for cosmetics, force the use of the quaternary ammonium compound, and the cosmetic itself, to pH's below 7. Below pH 7, the long chain amines exist as surface active salts which produce similar hair conditioning effects as surface active quaternary ammonium compounds. Above pH 7, the amine salts revert to their free organic amine state which cause them to loose their hair conditioning properties, to produce cosmetically unaesthetic odors and appearances, and to increase irritation to the skin and eyes.

On the other hand, long chain amine oxide surfactants have been freely used in acidic and alkaline cosmetics, toiletries and other consumer products. In alkaline products, amine oxide surfactants behave as nonionics; they bear neither positive nor negative molecular charges. The nonionic character allows them to be compatible with anionic ingredients in shampoos. Here, amine oxides can serve as foam contributors, foam stabilizes, viscosity enhancing agents, super fatting agents, etc. In nonionic and anionic hair conditioners, they can be employed as emulsifiers, thickeners and used for complementing typical fats, oils and waxes. The diversity of use of amine oxide surfactants are exemplified by the following disclosures.

In U.S. Pat. No. 3,990,991, aqueous shampoo-conditioner formulations are described comprising amphoteric, cryptoanionic and cationic surfactants. Amine oxides having surfactant properties are mentioned as useful cationic surfactants, although in the specific examples preferred quaternary ammonium compounds are employed in combination with an amine oxide. The pH of each such formulation is about 6.

In U.S. Pat. No. 4,007,261, conditioner compositions are described which consist essentially of an aqueous emulsion of an alkyl dimethyl amine oxide having from 16 to 22 carbon atoms in the alkyl chain, the pH of which compositions are preferably adjusted to between about 5.0 and 6.0. Specifically the invention encompasses pearlescent effects in such hair conditioners. However, it was found that such amine oxide formulations, namely the formulations having pH values described in this patent, did not provide adequate hair conditioning properties relative to quaternary ammonium surfactants. Augmentation of the amine oxide with quaternary ammonium compounds was required to impart good conditioning properties to formulations. See also, D&Cl, July 1981, pgs. 40–42, "Amine Oxides in Cosmetic Formulations", Klein, where "slightly acid pH" amine oxides were suggested as contributing to hair manageability.

U.S. Pat. No. 4,229,313 employs amine oxides as viscosity builders in cleaning and bleaching compositions for fabrics; both U.S. Pat. Nos. 4,4048,338 and 4,033,895 use amine oxides as counter-irritant ingredients in toiletry products to render them milder; U.S. Pat. No.

4,179,504 uses amine oxides as pharmacologically active ingredients in insecticidal and ovacidal preparations; U.S. Pat. No. 4,325,821 incorporates amine oxides into an improved froth flotation process to separate mineral ores; German Pat. No. 2,748,463 employs amine oxides as solubilizing agents for vitamin B derivatives in antiseborrheic products.

In acid media nonionic amine oxide surfactants acquire a positive charge through the inductive effects of hydrogen ions of the media. The amine oxides can behave cationic, however weakly cationic, since the positive charge produces less ionicity than that of quaternary ammonium salts of fatty amine salts. The positive charge, nevertheless, permits complete compatibility in cationic preparations and allows the cationicity of the amine oxide to support the cationicity of the dominant surfactant. An examination of the ingredient content of popular creme rinses, instant conditioners and balsams for hair sold on the market show that these products do not rely solely on amine oxides for conditioning. These acidic preparations employ quaternary ammonium surfactants and/or fatty amine salts, which are both strongly cationic, to produce hair conditioning. If amine oxides are present in the ingredient content, they are used for producing conditioning ancillary to the primary cationic surfactant as well as for other specific properties such as thickening, foaming, emulsification, etc. Amine oxide surfactants are recognized as not adsorbing to hair as strongly as quaternary ammonium surfactants and, therefore, do not produce as intense hair conditioning effects as quaternary ammonium salts.

Although it was known that amine oxides develop cationic properties, in other words a net positive charge, at low pH values for the reasons stated above, it has not been recognized that the cationic properties of amine oxides could be solely and usefully employed to condition hair in low pH media.

SUMMARY OF THE INVENTION

It has now been found that at pH values of about the isoelectric pH of hair protein or less, the relatively high molecular weight amine oxides described herein perform advantageously as desirable conditioning agents for hair.

The isoelectric point of hair, the state at which the positive and negative ionic charges of hair protein becomes balanced occurs under acid conditions. The exact point is not known with precision and investigators differ on the range of isoelectric point pH values; pH 3.3 to 4.5 by Cook and Smith, Appl. Polym. Symp. 18, 663 (1971), and more recently pH 2.45 to 3.17 by Parreira, Journal of Colloid and Interface Science, Vol. 75, No. 1 (1980). At the isoelectric point, protein carries a neutral charge.

An advantage occurs from inducing hair protein, keratin, to gather a neutral ionic charge, that is, to treat hair at its isoelectric point. At the isoelectric point, protein displays its greatest insolubility and greater ionic stability against chemical reaction. Hair treated at its isoelectric point pH so that hair protein can acquire an uncharged neutral state is conceivably rendered stronger than treatment at other pH's, although this is difficult to prove.

Accordingly, this invention provides a composition and means for taking advantage of the cationic properties of amine oxides which have been unapparent at low pH values.

It has been surprisingly found that within the pH range of, or about, the isoelectric point of hair or less, i.e., from about 3.8 to about 2.4, amine oxides acquire a sufficient positive charge to allow them to be substantially substantive onto the hair. The adsorbtion is to such an extent that it can allow the employment of amine oxides as the sole conditioning agent in creme rinse products. The rationale for such a phenomena is apparently obscure since at its isoelectric point, hair protein carries no polar charges and should not particularly adsorb the positive charged amine oxide molecules.

The precise mechanism is not known by which this unexpected adsorption and resulting conditioning effect at this low pH value takes place. However, it is speculated that the mechanism allows amine oxide surfactant to replace adsorbed hydrogen ions on the hair's surface. At the isoelectric point of hair, that is, at approximately a pH of from about 2.4 to about 3.8, all of the available negative sites on the hair's surface are filled by positively charged hydrogen ions, i.e., the hair becomes ionically neutral. It is believed that at these low pH's, amine oxide molecules gather a sufficient positive charge to allow them to compete for the sites held by the positive hydrogen ions on the surface of hair. Ion exchange takes place in which the amine oxide molecules substitute for the hydrogen ions. The ion exchange is accelerated by the surface activity of the amine oxide molecule which propel the amine oxide molecules to the surface of hair. Hence, it is the combination of surfactant activity and a significantly acquired positive charge through induction in acidic media that allow for the unusual and unexpected effects of amine oxides at about or less than the isoelectric point of hair.

This invention also offers the advantage of employing conditioning agents that are considered milder for the user than quaternary ammonium compounds. Amine oxides have been described as non-irritating in cosmetic systems and the present invention allows the use of such conditioning agents without addition of highly irritable quaternary ammonium salts.

Moreover, the conditioning balance of the hair conditioning composition of this invention may be easily modified by adjusting the pH of the formulation, the concentration of the amine oxide, or the physical or chemical nature of the amine oxide as governed by the properties of the long chain alkyl group(s). At lower pH values, the effectiveness of amine oxides are maximized because a greater proportion of the amine oxide molecules are converted to their cationic form. This enables reduced quantities of amine oxides to be used. Or, if less conditioning is desired, the pH of the compositions may be increased and/or the concentrations of the amine oxides may be reduced. One skilled in this art will readily understand how to achieve a balance between pH and amine oxide concentration for one's conditioning requirement.

DETAILED DESCRIPTION OF THE INVENTION

Amine oxides are the N-oxides of tertiary amines. They may be prepared by methods well known in the art, for example, by reaction of the corresponding tertiary amine with hydrogen peroxide.

One example of the amine oxides which are useful in preparing the conditioning composition of this invention include compounds having the formula:

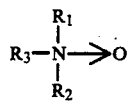

wherein $R_1$ and $R_2$ may be the same or different moities and are selected from lower ($C_1$-$C_4$) alkyl, alkoxy and hydroxyalkyl groups and $R_3$ is a moiety that contains at least 8 carbon atoms.

Examples of suitable oxides for use in this invention include lauryl dimethyl amine oxide, myristyl dimethyl amine oxide, cetyl dimethyl amine oxide, stearyl dimethyl amine oxide, oleyl dimethyl amine oxide, heptadecyl dimethyl amine oxide, behenyl dimethyl amine oxide, dimethyl cocamine oxide, dimethyl hydrogenated tallow amine oxide, bis (hydroxyethyl) cocamine oxide, bis (hydroxyethyl) tallow amine oxide, bis (hydroxypropyl) stearamine oxide, bis (hydroxymethyl) behenamine oxide, pentadecyl diethyl amine oxide, tridecyl dipropyl amine oxide, tridecyl bis (2-hydroxybutyl) amine oxide, heptadecyl bis(2-hydroxybutyl) amine oxide and tridecyloxypropyl bis (hydroxyethyl) amine oxide.

Generally, amine oxides having major alkyl chains or less than about 8 carbon atoms do not provide adequate hair conditioning and tend to be irritating to the user. Better conditioning results are obtained with single long chain amine oxides having 12 or more, and preferably 14-22 carbon atoms, in the long chain group and with double long chain amine oxides having as few as 8 carbons in their long chain groups. Preferred among the amine oxides is stearyl dimethyl amine oxide.

Other classes of suitable amine oxides include those of the formula:

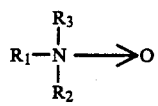

wherein $R_1$ and $R_2$ are the same or different moities and are selected from moieties of at least 8 carbons, and $R_3$ is a moiety selected from a lower ($C_1$-$C_4$) alkyl, alkoxy, or hydroxyalkyl group.

Examples of suitable amine oxides of this type include, dicoco methyl amine oxide, distearyl methyl amine oxide, dihydrogenated tallow methyl amine oxide, dicetyl methyl amine oxide, cetyl isocetyl methyl amine oxide, lauryl cetyl methyl amine oxide, dilinoleyl methyl amine oxide, disoya methyl amine oxide, diisostearyl methyl amine oxide, distearyl hydroxyethyl amine oxide, stearyl, isostearyl hydroxymethyl amine oxide, hexyl bis (2-hydroxyhexadecyl) amine oxide and distearyl hydroxypropyl amine oxide.

Another amine oxide class includes those amine oxides of the formula:

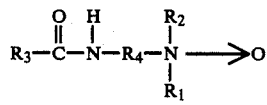

$R_1$ and $R_2$ are the same or different moieties and are selected from lower ($C_1$-$C_4$) alkyl, alkoxy and hydroxyalkyl groups, $R_3$ is a moiety containing an alkyl chain of at least 8 carbon atoms, and $R_4$ is a moiety selected from lower ($C_1$-$C_4$) alkyl group.

Examples of suitable amine oxides of this type include cocylamidopropyl dimethyl amine oxide, myristoylamidopropyl dimethyl amine oxide, stearoylamidoethyl dimethyl amine oxide, linoleoylamidopropyl dimethyl amine oxide, hydrogenated tallow amidoethyl bis (hydroxyethyl) amine oxide, palmitoylamidoethyl bis (hydroxypropyl) amine oxide, stearoylamidopropyl dimethyl amine oxide, and hydrogenated tallow amidopropyl dimethyl amine oxide.

Still another class of amine oxides includes those amine oxides of the formula:

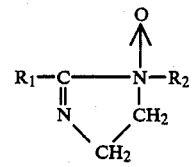

wherein $R_1$ is a moiety having an alkyl chain of at least 8 carbon atoms, and $R_2$ is a 2-hydroxyethyl or a derivative of 2-hydroxyethyl or a nonionic derivative of 2-aminoethyl.

Examples of suitable amine oxides of this class include oleyic imidazoline [1-hydroxyethyl-2-heptadecenyl-2-imidazoline-1-oxide], stearic imidazoline [1-hydroxyethyl-2-heptadecanyl-2-imidazoline-1-oxide], 1-acetylhydroxyethyl-2-tridecanyl-2-imidazoline-1-oxide, 1-acetylaminoethyl-2-tridecanyl-2-imidazoline-1-oxide, and 1-ethoxyethyl-2-pentadecanyl-2-imidazoline-1-oxide.

Yet another suitable class of amine oxides includes those of the formula:

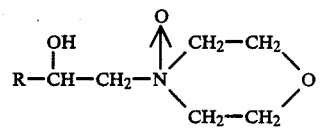

wherein R is a moiety having an alkyl chain of at least 6 carbon atoms.

Examples of suitable amine oxides of this class include N-2-hydroxynonyl-morpholine oxide, N-2-hydroxy-pentadecyl-morpholine oxide, and N-2-hydroxyheptadecyl-morpholine oxide.

A further class of amine oxides useful in the cationic hair conditioning compositions of this invention include those of the formula:

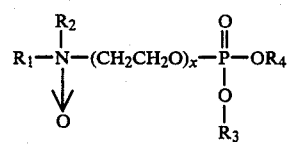

wherein $R_1$ is a moiety that contains an alkyl chain having at least 8 carbon atoms. $R_2$ is a moiety from the group consisting of

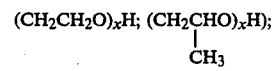

or an alkyl chain of at least 8 carbons; x is an integer from 1 to 30, and $R_{2=3}$ and $R_4$ are the same or different moieties and are selected from a lower ($C_1$–$C_4$) alkyl group.

Good results are obtained when the amine oxides are used at a concentration of between 0.5% and 10% by weight of the conditioner formulation. The preferred concentration is between about 1.5% and 6% of the amine oxide by weight of the hair conditioning composition.

The pH of the hair conditioning compositions is about or below the isoelectric point of hair protein. Specifically, the pH of the compositions of this invention is from about 3.8 to about 2.4. It has been preliminarily observed that amine oxides, and particularly stearyl dimethyl amine oxide, act to mitigate the potential for irritation resulting from the presence of acid in these compositions.

In general, the composition is prepared by admixing the amine oxide, water and sufficient acid, for example, hydrochloric acid, to reduce the pH within the aforesaid range of from about 3.8 to about 2.4. Other acids that may be used include phosphoric acid and those organic acids (acetic, citric, glycolic, etc.) that offer sufficient acidity to accommodate the low pH range.

Other ingredients may be added to the conditioning composition which serve known functions. For example, ethoxylated cetearyl alcohol which is an emulsifier, cetyl alcohol which is a viscosity builder and superfatting agent and other ingredients such as hydrolyzed protein, perfume, color and preservatives may be added as desired.

GENERAL FORMULATION AND PREPARATION

| General Formulation and Preparation | |
| --- | --- |
| Component | %, by weight |
| Long Chain Alkyl Amine Oxide | 6.0 |
| Cetyl-Stearyl Alcohol with 15 moles ETO | 0.5 |
| Cetyl Alcohol | 1.0 |
| Methyl Paraben | .2 |
| Propyl Paraben | 0.5 |
| Hydrolyzed Animal Protein (such as Collagen Hydrolyzate Cosmetic 50 by Maybrook) | .75 |
| FD&C Yellow #5 ($C_{16}H_{12}N_4O_9S_2$—3Na) | .0006 |
| Fragrance Oil | .75 |
| Concentrated HCl | 1.5 |
| Water | qS 100 |

In the above general information cetyl-stearyl alcohol with 15 moles ETO functions as an emulsifying agent; cetyl alcohol builds creamy structure of the emulsion and provides complimentary hair conditioning; the methyl and propyl parabens are preservatives; hydrolyzed animal protein serves as a complimentary conditioner and provides consumer appeal.

All the ingredients except the fragrance oil and acid are heated to 70°–75° C. and mixed to uniformity. The hydrochloric acid is mixed in and the preparation is slowly cooled to 60° C., then more quickly to 42° C. Fragrance is mixed in at 42° C. and the composition is cooled to room temperature. Moderate mixing takes place throughout the cooling process.

When stearyl dimethyl amine oxide was used as the specific amine oxide in the formula, the resulting product was a rich looking rheological lotion of 5,200 cps viscosity and pH of 2.6. When other linear amine oxides of lesser chain lengths were used, the lotions produced had lower viscosities. Additional quantities of a fatty alcohol were required in the formulations increase the viscosity of the resulting lotions. Some amine oxides such as oleyl dimethyl amine oxide, cocoamidopropyl dimethyl amine oxide, and oleic imidazoline amine oxide produced thin lotions. It was also observed that such amine oxides were totally soluble, by themselves, in water and were capable of producing clear hair conditioning products when used in the following formulation:

| Component | %, by weight |
| --- | --- |
| Water Soluble Alkyl Dimethyl Amine Oxide | 6.0 |
| Hydroxyethyl Cellulose (2% Sol'n, $H_2O$) | 50.0 |
| Nonoxynol-12 ($C_9H_{19}C_6H_4(OHC_2CH_2)_nOH$), (wherein n has an average value of 12) | 1.0 |
| Fragrance | 1.0 |
| Concentrated HCl | 1.5 |
| Water | qS 100 |

The clear product has a pH of 2.5 and a viscosity of 1,500 cps. It produced sudsing when applied to hair, suggesting its use as a shampoo in the application of a unitary product creme rinse conditioner and shampoo combination.

On the other hand, the dialkyl long chain amine oxides are more insoluble in water then the long chain monoalkyl amine oxides. When evaluated on hair in the above formula, the emulsion stability of the formula containing the di-long chain amine oxides was poor because of their low water solubility. A stabilized formula for the dialkyl long chain amine oxides was poor because of their low water solubility. A stabilized formula for the dialkyl long chain amine oxides was developed and products evaluated:

| Component | %, by weight |
| --- | --- |
| Di-long Chain Alkyl Methyl Amine Oxide | 1.5 |
| Polysorbate 85 (Polyoxyethylene (20) Sorbitan Trioleate) | 9.0 |
| Cetyl Stearyl Alcohol with 15 moles ETO | 2.0 |
| Cetyl Alcohol | 2.0 |
| Nonoxynol 12 | 0.5 |
| Fragrance | 0.5 |
| Concentrated HCl | qS pH 2.2–2.6 |
| Dye Blend | qS |
| Water | qS 100 |

All di-long chain amine oxides evaluated produced cosmetically elegant cremes and lotions. They all gave detangling effects on hair with the di-coco and di-stearyl giving exceptionally easy combing.

Translucent creme rinses can be formulated by combining water soluble and water insoluble amine oxides:

| Component | %, by weight |
| --- | --- |
| Stearyldimethyl amine oxide | 3.0 |
| Oleyl dimethyl amine oxide | 3.0 |
| Fragrance | 0.6 |
| Ucon LB-1715 (PPG-40 Butyl Ether (from Union Carbide)) | 0.4 |
| Hydroxyethyl Cellulose | 1.2 |
| Nonoxynol 12 (Nonylphenoxyether-12 ETO) | 0.6 |
| Concentrated HCl | 1.5 |
| Water | qS 100 |

This preparation was translucent, having a pH of 2.7 and a viscosity of 2,270 cps. In place of stearyl dimethyl amine oxide other insoluble varieties can be used, such as the cetyl, hydrogenated tallow and dicoco amine oxide analogs. In place of oleyl dimethyl amine oxide, water soluble amine oxides may be used such as the coco, cocamidopropyl, oleylimidazoline amine oxide analogs. All impart conditioning effects to hair.

The function of hydroxyethyl cellulose in these formulas is to thicken the preparation. Other thickening agents may be used such as hydroxypropyl methyl cellulose, hydroxypropyl cellulose, natural cellulose resins, etc. "Ucon" polymers as well as nonionic block polymers of the "Pluronic" type serve to adjust viscosity. Octylphenoxy ethers and nonylphenoxy ethers serve as emulsifiers and solubilizers for the fragrance and other oils. Other emulsifying agents may be used such as ethoxylated sorbitan esters (Polysorbate 65, Polysorbate 60) and polyethylene glycol ethers (PEG-400, PEG-600).

EXAMPLE 1

A. Procedure for Evaluation

A 2 gram, 10" long tress of double bleached hair is shampooed with a conventional shampoo, and reshampooed again to simulate a double shampoo typical of consumer use. The hair is rinsed thoroughly under the tap with tepid water. Five cc of a test hair conditioner is measured with a syringe and applied to the hair tress. The conditioner is worked into the hair tress for a minute and then the tress is rinsed with tepid water under the tap for one minute. The hair is touched, observed, combined, smelled and rated to a control shampooed tress without a conditioner application. Upon drying, the tress is treated again by touching, observing, combing and smelling.

Tests to determine the substantivity of the cationic amine oxide to hair protein have been conducted using the "Rubine Dye Test." The dye test for determining substantivity of cationics to hair demonstrates the degree of the adhesive nature of a cationic agent to hair during rinsing with water. Hair treated with a cationic conditioner will gather a rinse-fast stain when subjected to the dye; the coloration gathered on untreated hair is readily rinsed away. The dye complexes with positively charged surfactant residues on the hair forming a stain that resists rinsing from the hair. Pyrazole Fast Bordeau 2 BL was used in these tests in place of Rubine dye because Rubine dye has become unavailable. The amine oxides used in this invention produce a positive Rubine Dye Test response on tresses treated with formulations described herein.

The Rubine Dye Test employed a double bleached hair tress which was treated with a cationic conditioning product. After treatment, the tress was rinsed for exactly one minute under tepid tap water. The tress was then towel-dried and immersed in a 0.2% aqueous Pyrazol Fast Bordeau 2 BL dye solution for 10 seconds. Again, the tress was rinsed under the tap to remove excess dye solution from the hair. A residual red stain left on the hair indicated a substantive deposition of cationic amine oxide, whereas a free-rinsed control hair tress that had not been treated with the cationic conditioner prior to treatment with dye did not retain a red stain.

The hair conditioning delivered by the amine oxide compositions of this invention have properties that are variable and that which may be adjusted for in formulation. Since conditioning effects are relative to the needs of the user, It is a convenience to have adjustable features in formula development to suit the formulator's objectives. Certain users prefer to have as their major objective in hair conditioning excellent detangling of shampooed hair. Others prefer to have less detangling effectiveness but require that their hair feel natural, not overconditioned or heavily coated. Some users like to use clear products; others opaque cremes and lotions. Most users prefer to have their hair free of static charge to allow good manageability. The wide range of physical properties that various amine oxides offer are taken advantage of at or about the isoelectric point of hair protein to produce tailor made products that have features that satisfy the user.

As a corollary, it is difficult to measure the attributes of a hair conditioning product with only one parameter describing conditioning. In the evaluation of amine oxides and their formulations three parameters have been used to assess hair conditioning effects:

(1) The Rubine Dye Test serves to demonstrate the substantivity of cationic ingredients in hair conditioners. The substantive coating, that shows red with Rubine dye, is composed of positive charged and/or polarized molecules which tend to conduct ions or electrons (the localized accumulation of such ions or electrons is the cause of static charges). A positive Rubine Dye Test, therefore indicates that because of the substantive coating on the hair which is conductive, any accumulating ions or electrons will be mobile and any electrostatic charges therefrom are readily dissipated. Hence, the disadvantages to manageability of hair from static electricity are nullified.

(2) Touching hair serves to inform the user the state of conditioning in one's hair. The feeling is totally subjective, varying among individuals according to personal prefernces. Some prefer light texture, approaching a natural or unconditioned effect; others prefer the tactile demonstration of conditioning provided by a significant coating of fatty material. In the laboratory evaluation of the "touch" parameter, using a range of 1 to 10, 10 signified a clean feeling, the absence of coating which is apparently present (Rubine Dye test) and which can offer other advantages; 1 signified a maximum, heavily conditioned coating that can be felt with the fingers. Either effects, a clean feeling or a definitive "conditioned" coating, can be desirable depending on the users perspective.

(3) The ease rendered in combing wet hair after shampooing is perhaps the single most important benefit of creme rinse products. Immediately after shampooing, hair is usually left matted and difficult to comb through. Damage to the hair structure usually results upon combing or brushing at this stage because of the intense friction produced on the tangled hair. Furthermore, pulling and stretching the hair during wet combing results in the weakening of its tensile strength, some degree of hair breakage and causes pain and discomfort to the individual. The application of a creme rinse balsam or other hair conditioning treatment provides a lubricant coating to the hair shaft that reduces and minimizes the combing effort. The user is thus spared the discomfort of combing tangled and snarled hair. In laboratory evaluation, the effectiveness of a conditioner application in providing easy combing after a shampoo treatment is rated on a 1 to 10 scale. A rating of 10 indicates easy wet combing comparable to the effects of a leading commercial hair conditioner based upon quaternary ammonium surfactants; a rating of 1 indicates the base state of combing hair after shampooing with a detergent cleanser and without a hair conditioner application.

B. The Hair Conditioning Compositions

The hair conditioning formulations were made as described above and tested.

C. The Results

The results of the tests are shown in the table below:

| Conditioning Agents | Rubine Dye Test | Touch Parameter | Hair Detangling Effectiveness |
|---|---|---|---|
| Lauryl dimethyl amine oxide | + | 10 | 2 |
| Cocoamidopropyl dimethyl amine oxide | + | 9.5 | 5 |
| Myristyl dimethyl amine oxide | + | 9 | 4 |
| Stearyl dimethyl amine oxide | + | 7 | 10 |
| Cetyl dimethyl amine oxide | + | 8 | 8 |
| Oleyl dimethyl amine oxide | + | 10 | 5 |
| Hydrogenated tallow dimethyl amine oxide | + | 7.5 | 6 |
| Cocoamine dimethyl amine oxide | + | 9.5 | 3 |
| Coco bis (hydroxyethyl) amine oxide | + | 10 | 3 |
| Tallow bis (hydroxyethyl)amine oxide | + | 7 | 3 |
| Oleic imidazoline amine oxide | + | 10 | 3 |
| Quaternary ammonium salt (Commercial Product Control) | + | 3 | 10 |

EXAMPLE 2

This example demonstrates the criticality of the pH range of the hair conditioning composition herein and the improvements in wet combing, dry combing and manageability attributable to the pH range herein compared with the higher pH of a similar hair conditioning composition disclosed in U.S. Pat. No. 4,007,261.

A. Procedure for Evaluation (1) 2.5±0.5 g., 10 inch hair swatches are prepared using consistent and uniform hair types (Virgin, Bleached, Grey, etc.).

(2) The hair tresses are collectively shampooed with a 15% active sodium lauryl sulfate solution, using an excess quantity of detergent solution. The hair tresses are carefully handled to avoid excessive tangling during shampooing and are then rinsed free and rendered clean with 40° C. tap water. This process is repeated to simulate a double shampoo application. All test hair tresses are presented in an equivalent clean and "degreased" state.

(3) Individual hair tresses are separated and tagged for test application. Two cc. of a test conditioner preparation (excess) is applied to a cleaned, wet tress with a syringe. The conditioner is worked through the hair for one minute with downward strokes of the fingers. The tress is rinsed thoroughly clean under 40° C. tap water for one minute. All test conditioners are treated equivalently. An untreated tress serving as a control is used as a point of reference.

A rating system of 1 to 10 is used in which 1 represents the base state of untreated, difficult-to-manage hair and 10 represents optimum conditioned hair. The rating scale may be used as follows:

10—Highest optimum rating, excellent.
9—Good Excellent.
8—Good.
7—Fair-Good.
6—Average.
5—Mediocre.
4—Fair-Poor.
3—Poor.
2—Very Poor.
1—Void of Positive Effects.

A two unit spread is considered readily perceptible and significant.

The evaluation procedure is as follows:

(1) Combing: Hair is combed through, at first, in the wet state then in the dry state, using the fine teeth of a #400 "Cleopatra" comb. Prior to wet combing, excess water is squeezed from the tress in order to simulate towel-dry hair. A rating number is ascribed relative to that of a control tress.

(2) Fly-away: The degree of static charge (on dry hair only) is observed by combing a tress quickly 10 strokes with the coarse teeth of a #400 Cleopatra comb. A rating is assigned relative to a control tress.

(3) Manageability is assessed relative to a control by observing its behavior pattern. A rating number is given.

B. The Hair Conditioning Compositions

The following preparations (in which all amounts are given in percent by weight) were employed in the conditioning of individual hair tresses which has been collectively shampooed as described in the protocol, supra.

| Test Preparation | Water (deionized) | Amine Oxide | pH (adjusted with phosphoric acid) |
|---|---|---|---|
| 1 (control) | 100 | — | — |
| 2 (Example 1 of U.S. Pat. No. 4,007,261) | 76 | 24 (25% active stearyl dimethyl amine oxide) | 5.5 |
| 3 (This invention) | 76 | 24 (25% active stearyl dimethyl amine oxide) | 2.7 |
| 4 (U.S. Pat. No. 4,007,261) | 88 | 12 (50% active oleyl dimethyl amine oxide) | 5.5 |
| 5 (This invention) | 88 | 12 (50% active oleyl dimethyl amine oxide) | 2.7 |

The performance characteristics of these five (5) preparations were evaluated in accordance with the foregoing procedure.

C. The Results

| Evaluation | 1 control | Test Preparation 2 Example 1 U.S. Pat. No. 4,007,261 | 3 This Invention | 4 U.S. Pat. No. 4,007,261 | 5 This Invention |
|---|---|---|---|---|---|
| Combing-wet | 2 | 2 | 6 | 6 | 8 |
| Combing-dry | 4 | 5 | 7 | 6 | 8 |
| Fly-away | 5 | 9 | 9 | 9 | 9 |
| Managability | 3 | 5 | 7 | 7 | 8 |

These data show that in the wet combing, dry combing and manageability evaluations, hair conditioning compositions in accordance with the amended claims significantly, outperformed the comparable compositions described in U.S. Pat. No. 4,007,261. These results were wholly unexpected and there is nothing in U.S. Pat. No. 4,007,261 which would have suggested them.

It will be understood that it is intended to cover all changes and modifications of the examples of the invention herein chosen for the purpose of illustration which do not constitute departures from the spirit and scope of the invention.

What is claimed is:

1. A cationic hair conditioning composition comprising:
   (a) an amine oxide of the formula:

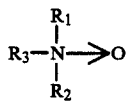

wherein $R_1$ and $R_2$ are the same or different moieties and are selected from lower ($C_1$-$C_4$) alkyl, alkoxy and hydroxy alkyl groups, and $R_3$ is an alkyl group containing 8 to 22 carbon atoms; and
   (b) water and sufficient acid to provide a pH for said composition of from about 3.8 to about 2.4 and an amine oxide concentration from about 0.5% to about 10% based on the total weight of said hair conditioning composition.

2. The cationic hair conditioning composition of claim 1 wherein said amine oxide concentration is from about 1.5% to about 6% based on the total weight of said hair conditioning composition.

3. The cationic hair conditioning composition of claim 1 wherein said amine oxide is stearyl dimethyl amine oxide.

4. The cationic hair conditioning composition of claim 1 wherein said amine oxide is oleyl dimethyl amine oxide.

5. A cationic hair conditioning composition comprising:
   (a) an amine oxide of the formula:

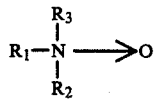

wherein $R_1$ and $R_2$ are the same or different moieties and are selected from moieties that contain at least 8 carbon atoms, and $R_3$ is a moiety selected from a lower ($C_1$-$C_4$) alkyl, alkoxy or hydroxy alkyl group; and
   (b) water and sufficient acid to provide a pH for said composition of from 3.8 to about 2.4 and a amine oxide concentration from about 0.5% to about 10% based on the total weight of said hair conditioning composition.

6. The cationic hair conditioning composition of claim 5 wherein said amine oxide concentration is from about 1.5% to about 6% based on the total weight of said hair conditioning composition.

7. The cationic hair conditioning composition of claim 5 wherein said amine oxide is distearyl monomethylamine oxide.

8. A cationic hair conditioning composition comprising:
   (a) an amine oxide of the formula:

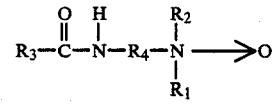

wherein $R_1$ and $R_2$ are the same or different moieties and are selected from lower ($C_1$-$C_4$) alkyl, alkoxy and hydroxy alkyl groups, $R_3$ is a moiety containing an alkyl chain of at least 8 carbon atoms, and $R_4$ is a moiety selected from lower ($C_1$-$C_4$) alkyl groups; and,
   (b) water and sufficient acid to provide a pH for said composition of from about 3.8 to about 2.4 and an amine oxide concentration from about 0.5% to about 10% based on the total weight of hair conditioning composition.

9. The cationic hair conditioning composition of claim 8 wherein said amine oxide concentration is from about 1.5% to about 6% based on the total weight of said hair conditioning composition.

10. The cationic hair conditioning composition of claim 8 wherein said amine oxide is cocoylamidopropyl dimethyl amine oxide.

11. A cationic hair conditioning composition comprising:
    (a) an amine oxide of the formula:

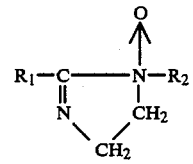

wherein $R_1$ is a moiety having an alkyl chain of at least 8 carbon atoms, and $R_2$ is a moiety selected from the group consisting of 2-hydroxyethyl, a derivative of 2-hydroxyethyl, and a nonionic derivative of 2-amino ethyl; and
    (b) water and sufficient acid to provide a pH for said composition of from about 3.8 to about 2.14 and an amine oxide concentration from about 0.5% to about 10% based on the total weight of said hair conditioning composition.

12. The cationic hair conditioning composition of claim 11 wherein said amine oxide concentration is from about 1.5% to about 6% based on the total weight of said hair conditioning composition.

13. The cationic hair conditioning composition of claim 11 wherein said amine oxide is oleic imidazoline amine oxide.

14. A cationic hair conditioning composition comprising:
    (a) an amine oxide of the formula:

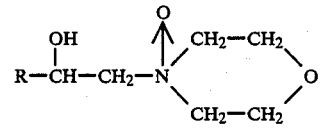

wherein R is a moiety having an alkyl chain of at least 6 carbon atoms; and (b) water and sufficient acid to provide a pH for said composition of from about 3.8 to about 2.4 and an amine oxide concentration from about 0.5% to 10% based on the total weight of said hair conditioning compositions.

15. The cationic hair conditioning composition of claim 14 wherein said amine oxide concentration is from about 1.5% to about 6% based on the total weight of said hair conditioning composition.

16. A cationic hair conditioning comprising:
(a) and amine oxide of the formula:

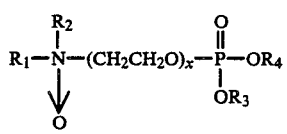

wherein $R_1$ is a moiety that contains an alkyl chain having at least 8 carbon atoms; $R_2$ is a moiety from the group consisting of

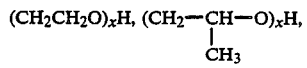

and an alkyl chain of at least 8 carbon atoms; x is an integer from 1 to 30; and $R_3$ and $R_4$ are the same or different moieties and are selected from a lower ($C_1$-$C_4$) alkyl group; and (b) water and sufficient acid to provide a pH for said composition of from about 3.8 to about 2.4 and an amine oxide concentration from about 0.5% to about 10% based on the total weight of said hair conditioning composition.

17. The cationic hair conditioning composition of claim 16 wherein said amine oxide concentration is from about 1.5% to about 6% based on the total weight of said hair.

* * * * *